United States Patent
Ramsey

(10) Patent No.: US 10,610,084 B2
(45) Date of Patent: Apr. 7, 2020

(54) INSTRUMENT TIP PROTECTOR

(71) Applicant: Meditech Endoscopy LTD, Chesterfield, Derbyshire (GB)

(72) Inventor: Peter Ramsey, Chesterfield (GB)

(73) Assignee: MEDITECH ENDOSCOPY LTD, Chesterfield, Derbyshire (GB)

( * ) Notice: Subject to any disclaimer, the term of this patent is extended or adjusted under 35 U.S.C. 154(b) by 361 days.

(21) Appl. No.: 15/518,958

(22) PCT Filed: Oct. 12, 2015

(86) PCT No.: PCT/GB2015/052978
§ 371 (c)(1),
(2) Date: Apr. 13, 2017

(87) PCT Pub. No.: WO2016/059383
PCT Pub. Date: Apr. 21, 2016

(65) Prior Publication Data
US 2017/0224191 A1    Aug. 10, 2017

(30) Foreign Application Priority Data

Oct. 14, 2014 (GB) .................................. 1418173.9
Jul. 28, 2015 (GB) .................................. 1513260.8

(51) Int. Cl.
*A61B 1/00* (2006.01)
*G02B 23/24* (2006.01)

(52) U.S. Cl.
CPC ........ *A61B 1/0008* (2013.01); *A61B 1/00059* (2013.01); *A61B 1/00131* (2013.01); *A61B 1/00144* (2013.01); *G02B 23/2476* (2013.01)

(58) Field of Classification Search
CPC .................................................. A61B 1/0008
(Continued)

(56) References Cited

U.S. PATENT DOCUMENTS

| 4,773,394 A |   | 9/1988 | Reichstein et al. |
| 5,415,157 A | * | 5/1995 | Welcome ............... A61B 46/10 |
|   |   |   | 206/571 |

(Continued)

FOREIGN PATENT DOCUMENTS

| CN | 1692872 A | 11/2005 |
| JP | 2007075281 A | 3/2007 |

(Continued)

*Primary Examiner* — John P Leubecker
*Assistant Examiner* — Shankar Raj Ghimire
(74) *Attorney, Agent, or Firm* — Hayes Soloway PC

(57) ABSTRACT

This invention relates to a tip protector for an instrument such as an endoscope or borescope. A tip protector device for an instrument comprises a guard portion engagable with a tip of an instrument, the guard portion including an abutment surface arranged to contact the tip such that a part of the guard portion extends distally of an end face of the tip, and the guard portion being configured to prevent contact between the guard portion and a central portion of the end face; gripping members arranged to grip a part of a shaft of the instrument; a first connection member; and a second connection member, the first and second connection members being movable relative to each other between a first, disengaged position in which the tip of the instrument can be inserted into and removed from the tip protector device, and a second, gripping position in which the gripping members contact and grip the shaft of the instrument, wherein, the first and second connection members are biased in the first or the second position.

22 Claims, 10 Drawing Sheets

(58) Field of Classification Search
USPC .......................................................... 600/127
See application file for complete search history.

(56) References Cited

U.S. PATENT DOCUMENTS

| | | | | |
|---|---|---|---|---|
| 5,645,350 | A * | 7/1997 | Jang | A61B 1/00142 374/158 |
| 5,779,046 | A | 7/1998 | Plakos | |
| 6,457,583 | B1 | 10/2002 | Tee et al. | |
| 6,592,558 | B2 * | 7/2003 | Quah | A61M 39/284 128/912 |
| 6,793,399 | B1 * | 9/2004 | Nguyen | G01M 11/088 356/241.1 |
| 6,986,584 | B2 | 1/2006 | Benner | |
| 7,007,797 | B1 | 3/2006 | Ruccolo | |
| 9,078,781 | B2 * | 7/2015 | Ryan | A61F 2/958 |
| 9,829,113 | B2 * | 11/2017 | Brugger | B29C 37/0003 |
| 2005/0162643 | A1 * | 7/2005 | Karpen | G02B 23/2476 356/237.1 |
| 2007/0212926 | A1 | 9/2007 | Nakaura et al. | |
| 2008/0135433 | A1 | 6/2008 | Weis et al. | |
| 2009/0221872 | A1 | 9/2009 | Liddle et al. | |
| 2010/0125164 | A1 * | 5/2010 | LaBombard | A61B 1/00087 600/104 |
| 2010/0243493 | A1 | 9/2010 | Harris | |
| 2010/0249510 | A1 * | 9/2010 | Yamada | A61B 1/00135 600/121 |
| 2010/0261967 | A1 * | 10/2010 | Pacey | A61B 1/00103 600/186 |
| 2012/0035553 | A1 * | 2/2012 | Lombardo | A61M 39/284 604/250 |
| 2012/0232497 | A1 * | 9/2012 | Singh | A61M 39/284 604/250 |
| 2013/0018330 | A1 * | 1/2013 | Baid | A61M 5/3273 604/263 |
| 2013/0066280 | A1 * | 3/2013 | Wallin | A61M 39/284 604/250 |
| 2013/0267777 | A1 * | 10/2013 | Avitsian | A61B 1/00135 600/123 |
| 2014/0376987 | A1 * | 12/2014 | Rolion | B43K 7/12 401/111 |

FOREIGN PATENT DOCUMENTS

| | | |
|---|---|---|
| JP | 2007330421 A | 12/2007 |
| RU | 2156104 C2 | 9/2000 |
| SU | 1451634 A1 | 1/1989 |
| WO | 2006130730 A2 | 12/2006 |
| WO | 2009150186 A1 | 12/2009 |
| WO | 2011075509 A1 | 6/2011 |

* cited by examiner

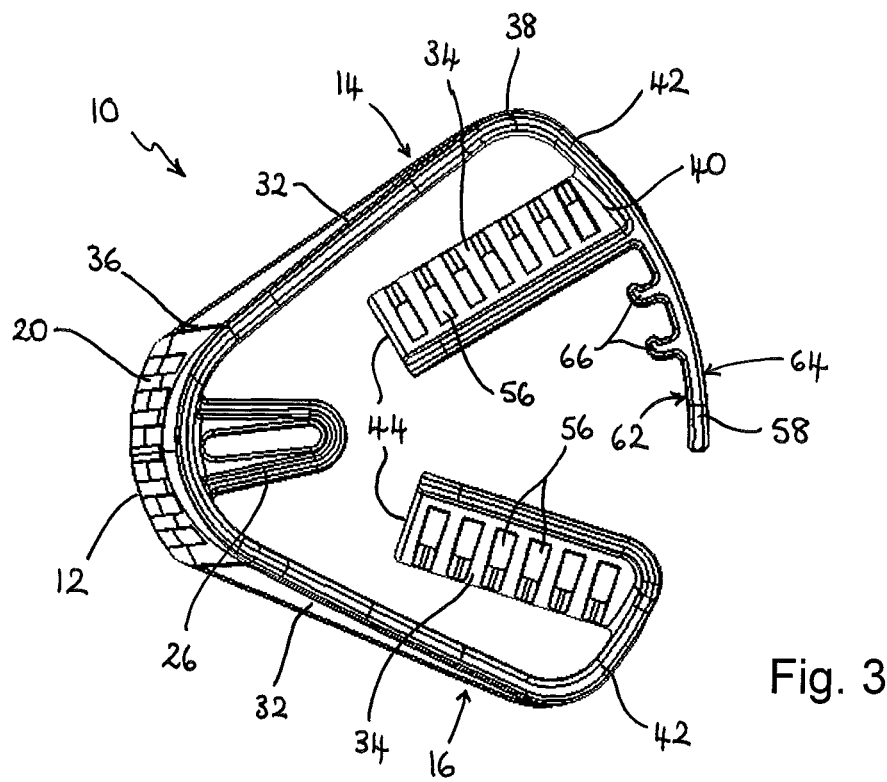
Fig. 3
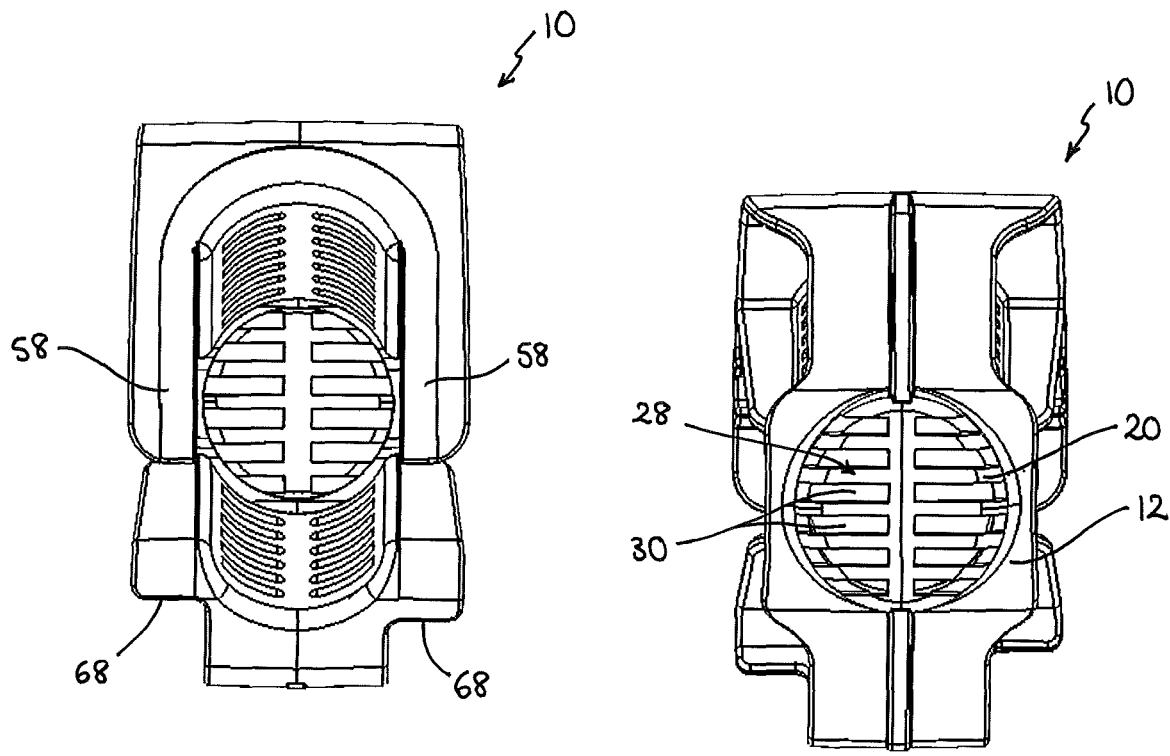
Fig. 4
Fig. 5

INSTRUMENT TIP PROTECTOR

BACKGROUND a. Field of the Invention

This invention relates to a tip protector for an instrument such as an endoscope or borescope, to an assembly comprising a tip protector and an endoscope or borescope, and to a blank for use in the construction of a tip protector.

b. Related Art

An endoscope or borescope is used to image cavities or other interior spaces that are not easily accessible and where direct observation of the space is not possible.

An endoscope or other similar elongate optical probe comprises an elongate insertion shaft having a distal tip. An objective lens is provided at the distal tip and an optical transmission system is provided within the shaft of the endoscope to transmit images from the tip to a user of the device. Typically the optical transmission system will include optical fibres and/or lens assemblies.

The shaft and tip are typically also configured to enable illumination of the area around the tip of the endoscope, and to allow other instruments to extend through the shaft and from the tip, for example biopsy forceps in the case of some medical endoscopes. Accordingly the tip of an endoscope can be very complex, very delicate and, therefore, relatively expensive.

It is thought that for every endoscope being used in a hospital setting, at least half may be unavailable for use due to repair. Damaged endoscopes can be expensive to repair, can disrupt a facility's capacity to provide endoscopy services, and can potentially compromise patient safety. Furthermore, it is believed that approximately 70% of endoscope damage may be attributed to improper handling.

During cleaning and storage of the endoscope or borescope, and additionally during sterilisation of medical endoscopes it is, therefore, desirable to protect the tip as much as possible from damage. A number of prior art devices are known, especially for use in medical applications, however, each of these devices has disadvantages.

A first device comprises a generally cylindrical body made of sponge or soft foam and having a central opening for receiving the tip of the endoscope. The device, therefore, provides cushioning around the tip but the foam is also potentially capable of absorbing moisture from the tip. This absorption of moisture can cause the sponge or foam to harbour microorganisms that may contaminate the endoscope.

A second device comprises an expandable plastic mesh sleeve that is configured to fit over the tip of the endoscope. The configuration of the mesh sleeve provides a degree of resilience protecting the tip from knocks. The mesh sleeve, however, can be difficult to put on and remove from the tip of the endoscope, which may lead to damage to the tip. Furthermore, the mesh sleeve contacts the endoscope tip over a relatively large area hindering the drying and aeration of the endoscope tip during cleaning and storage.

It is an object of the present invention to provide an improved tip protector device that overcomes at least some of the disadvantages of prior art devices.

SUMMARY OF THE INVENTION

According to a first aspect of the present invention there is provided a tip protector device for an instrument, the instrument comprising an elongate shaft having a distal tip and said tip including an end face, and the tip protector device comprising:

a guard portion engagable with said tip, the guard portion including an abutment surface arranged to contact the tip such that a part of the guard portion extends distally of said end face, and the guard portion being configured to prevent contact between the guard portion and a central portion of the end face;

gripping members arranged to grip a part of the shaft of the instrument;

a first connection member; and a second connection member, the first and second connection members being movable relative to each other between a first, disengaged position in which said tip of the instrument can be inserted into and removed from the tip protector device, and a second, gripping position in which the gripping members contact and grip the shaft of the instrument, wherein, the first and second connection members are biased in the first or the second position.

The tip protector device is designed to protect the delicate optics of an instrument such as an endoscope while permitting air flow around the tip to prevent the formation of a biofilm on the instrument. Furthermore, the protector device is designed to be easy to attach to and remove from the tip of the instrument.

To aid air flow and protect the delicate tip and end face of the instrument, the gripping members preferably grip the shaft at a distance from the end face.

Preferably the protector device is a unitary body. The protector device is preferably made from a plastics material and may be injection moulded.

The guard portion preferably comprises at least one aperture. In some embodiments the guard portion may include a plurality of apertures. In some embodiments each of the first and second connection members includes at least one aperture. The provision of apertures increases the air flow around the tip of the instrument.

In these embodiments in which the connection members are biased in the first position the protector device preferably further comprises latching means configured to retain the first and second arm portions in the second position. A first part of the latching means may be provided on the first connection member and a second part of the latching means may be provided on the second connection member. In some embodiments the latching means may comprise a detent provided on one of the first or second connection members and a shoulder provided on the other one of the first or second connection members for engagement with said detent. In other embodiments the latching means may comprise interengaging teeth.

In some embodiments the first connection member may extend from a first side of the guard portion and the second connection member may extend from a second side of the guard portion. In these embodiments a first part of the latching means may be located at an end of the first connection member furthest from the guard portion and a second part of the latching means may be located at an end of the second connection member furthest from the guard portion. In some embodiments the end of the second connection member preferably comprises two leg members, the leg members being spaced apart so as to receive the shaft of the instrument between them. In these embodiments the first part of the latching means may be located on the leg members.

A first gripping member preferably extends from an end of the first connection member and a second gripping member preferably extends from an end of the second connection member. Each of the gripping members preferably extends from the end of the respective connection member in a direction towards the guard portion. Each of the gripping members may be semi cylindrical.

In some embodiments the first connection member may extend between a first gripping member at a first end and a first part of the latching means at a second end and the second connection member may extend between a second gripping member at a first end and a second part of the latching means at a second end. In these embodiments a bridging member preferably joins the first and second connection members at their respective first ends so that the first and second gripping members are spaced apart for receiving the shaft of the instrument therebetween. In these embodiments the guard portion is preferably located at or proximate the second end of the first connection member. Each of the gripping members preferably comprises a first portion that extends in a direction substantially towards the second end of the respective connection member and a second portion that extends in a direction substantially opposite to that of the first portion.

The guard portion may comprise a collar configured, in use, to surround the tip of the instrument. In some embodiments the second end of the second connection member may comprise two leg members, the leg members being spaced apart so as to receive the collar between them. The second part of the latching means is preferably located on the leg members.

The tip protector device may further comprise a tab attached to the first or the second connection member. The tab is preferably arranged to conceal the latching means when the first and second connection members are in the second position. Furthermore, the tab is preferably configured such that the tab must be broken to allow the latching means to be disengaged to move the first and second connection members to the first position.

The tip protector device preferably further comprises distinguishing means. In some embodiments a first distinguishing means may be provided on the tab and a second distinguishing means may be concealed by the tab when the first and second connection members are in the second position, the second distinguishing means being revealed when the tab is broken.

In some embodiments the first and second arm portions are biased in the second position.

In order to prevent damage to the end face of the instrument it is preferable if the guard portion is shaped such that, in use, the guard portion does not contact said end face of the instrument. In some embodiments the guard portion comprises a curved cover plate which, in use, extends across said end face of the instrument.

In some preferred embodiments of the invention the device is assembled from a flat sheet of material that is folded to form the device.

A blank used to construct the protector device may comprise a first arm panel including an aperture sized to receive said tip of the instrument; a second arm panel including an aperture sized to receive said tip of the instrument; a first guard panel; a second guard panel; a first fold line between the first arm panel and the second arm panel; a second fold line between the second arm panel and the first guard panel; and a third fold line between the first guard panel and the second guard panel, the third fold line being substantially parallel to both of the first and second fold lines.

According to a second aspect of the present invention there is provided an assembly comprising:
 a tip protector device according to the first aspect of the invention; and
 an instrument, the instrument comprising an elongate shaft having a tip and said tip including an end face, and the tip protector device being engaged with the tip of the instrument.

Typically the instrument will be an endoscope or a borescope.

BRIEF DESCRIPTION OF THE DRAWINGS

The invention will now be described further by way of example only and with reference to the accompanying drawings, in which:

FIG. 3 is a side view of the protector device of FIG. 1;

FIG. 4 is an end view from a first end of the protector device of FIG. 1;

FIG. 5 is an end view from a second end of the protector device of FIG. 1;

DETAILED DESCRIPTION

Figure 1:
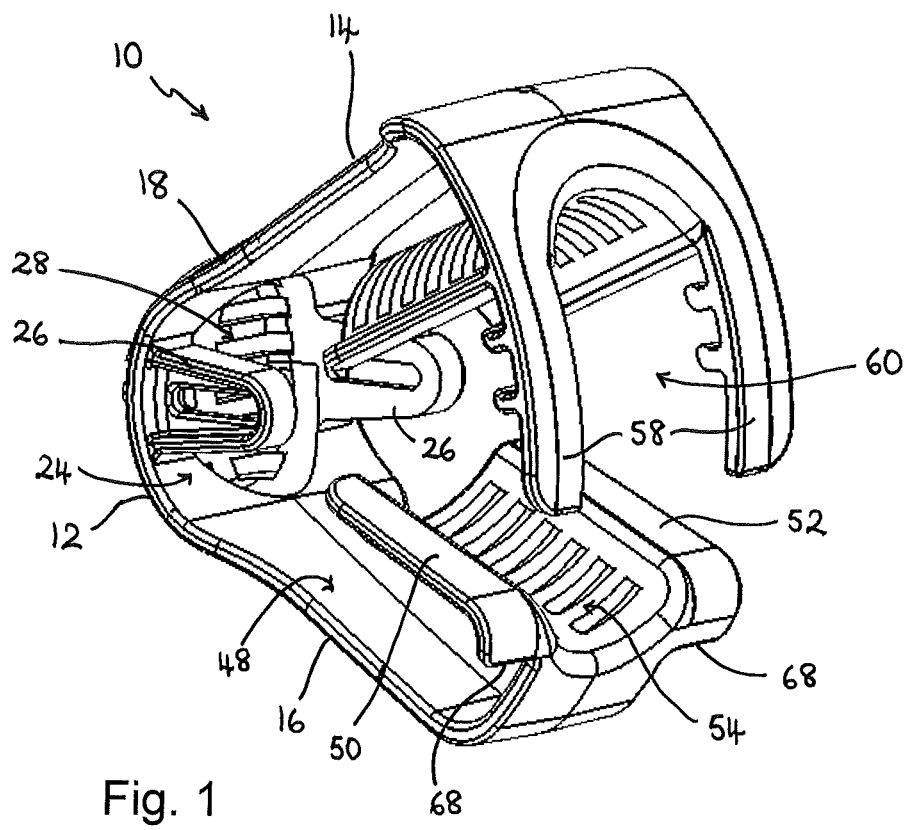
FIG. 1 is a perspective view of a protector device according to a first preferred embodiment of the present invention.
Figure 2:
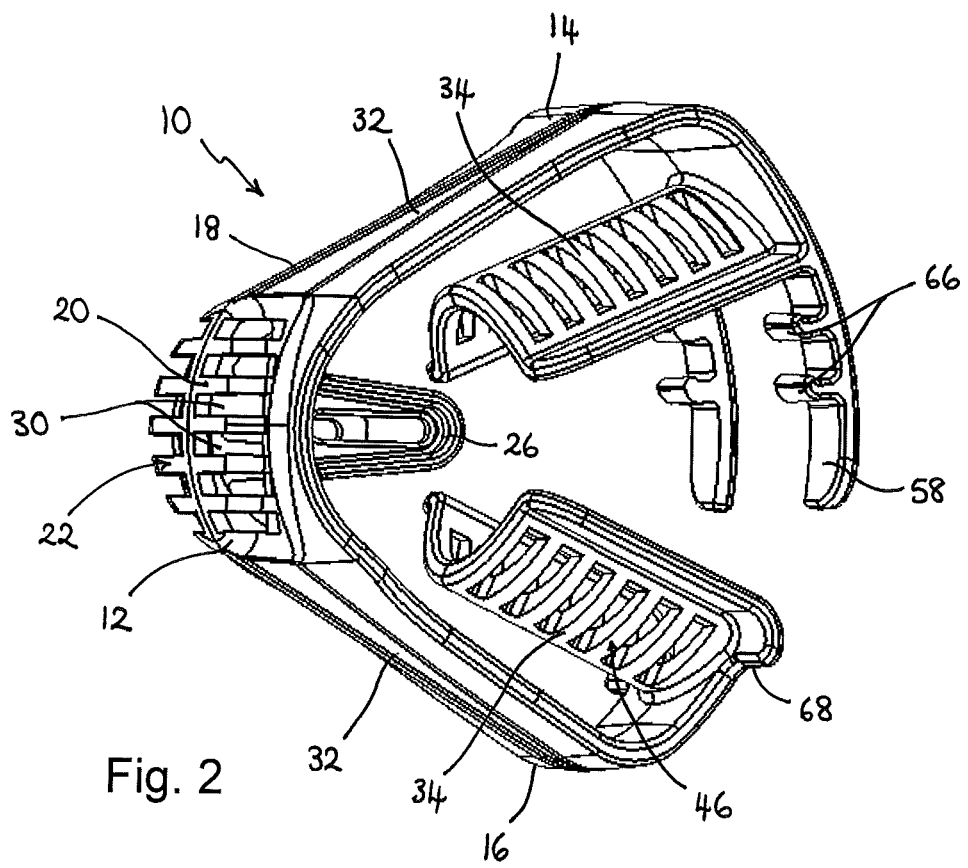
FIG. 2 is another perspective view of the protector device of FIG. 1.

The present invention concerns a device for protecting the distal tip of an endoscope or similar instrument. By similar instrument it is meant any instrument having an elongate shaft and a distal tip where it would be desirable or beneficial to protect the tip from damage. Typically these instruments will be optical instruments having a lens or part of a lens system at the distal tip. Such instruments may be, but are not limited to, borescopes such as those used in industrial applications or endoscopes such as those used in medical applications. Endoscopes may include scopes such as colonoscopes, gastroscopes, esophagoscopes and sigmoidoscopes. It will be understood that references in the following description to an endoscope also encompasses a borescope and similar instruments.

An endoscope 1 includes an elongate shaft or insertion tube 3 having a distal tip 5. The shaft or insertion tube 3 may be flexible or rigid, depending on the specific application. Typically the distal tip 5 of the endoscope 1 will include an end face 7 that is planar and is substantially perpendicular to a longitudinal axis of the shaft 3; however, in some endoscopes the end face may be curved, or the tip may be tapered such that the end face is at an angle of less than 90° to the longitudinal axis.

The tip protector devices of the present invention are configured to engage with and attach to the tip 5 or shaft 3 of the endoscope 1 so as to protect the tip 5 and, in particular, to protect the end face 7 of the tip 5 from potential damage.

A first embodiment of a tip protector device 10 according to the invention is shown in FIGS. 1 to 7. The protector device 10 comprises a guard portion 12, a first connection member or arm 14 and a second connection member or arm 16. In this example the protector device 10 is of unitary, one-piece construction, such that the guard portion 12, first arm 14 and second arm 16 are parts of a unitary main body 18 of the device 10.

The guard portion 12 comprises a cover plate 20 having a first, front face 22 and an opposing second, rear face 24. In this embodiment the cover plate 20 is curved; however, the cover plate may be planar or may comprise two or more sections at an angle to each other. Two fingers 26 extend from the rear face 24 of the cover plate 20. The two fingers 26 are spaced apart from each other thereby defining a gap between them sized to receive the tip 5 of an endoscope 1, as shown most clearly in FIG. 6.

When a tip 5 of an endoscope 1 is received between the two fingers 26, the cover plate 20 extends across the end face 7 of the tip 5. In this way the cover plate 20 protects the end face 7 from damage that may occur during transportation or storage of the endoscope 1. The guard portion 12, and in particular the cover plate 20, is shaped such that minimal or no contact is made between the guard portion 12 and the end face 7 of the tip 5 when the tip 5 of the endoscope 1 is received between the fingers 26. In particular, the curvature of the cover plate 20 means that the guard portion 12 does not contact a central region of the end face 7. A peripheral region of the rear face 24 of the cover plate 20 may provide an abutment surface against which the tip 5 of the endoscope 1 abuts when the tip 5 is fully inserted into the device 10.

At least a central region 28 of the cover plate 20 includes a plurality of apertures 30. The central region 28 will typically extend across an area between the two fingers 26. Accordingly, when an endoscope tip 5 is located between the fingers 26, the apertures 30 allow liquids such as water to drain away from the tip 5.

The fingers 26 and a part of each of the arms 14, 16 proximate the guard portion 12 prevent knocks to the side of the tip 5 of the endoscope 1 when the tip is correctly positioned within the protector device 10 with the end face 7 of the tip located proximate or within the guard portion 12.

The first and second arms 14, 16 extend from the cover plate 20 such that the cover plate 20 and arms 14, 16 define a generally U-shaped part of the main body 18.

Each of the first and second arms 14, 16 includes an outer wall portion 32 and an inner collar portion 34. A first end 36 of the wall portion 32 is connected to the guard portion 12, and an opposing second end 38 of the wall portion 32 is connected to a respective second end 40 of the collar portion 34 by means of a bridging portion 42. The collar portion 34 extends from its second end 40 in a direction substantially towards the guard portion 12 and a first end 44 of the collar portion 34 is a free end 44. The connection between the wall portion 32 and the collar portion 34 is such that a space is defined between an outer surface 46 of the collar portion 34 and an inner surface 48 of the wall portion 32.

Each of the collar portions 34 has a semi-annular cross-sectional shape perpendicular to an axis extending between the first and second ends 44, 40 of the collar portion 34. In this way, each of the collar portions 34 has a half-pipe shape terminating in first and second side edges 50, 52, which in this embodiment are substantially parallel to each other. The outer surface 46 of the collar portion has a convex curvature and an inner surface 54 has a concave curvature. In this embodiment of the protector device 10, the collar portion 34 is elongate such that a length of the collar portion 34 between the first and second ends 44, 40 is greater than the diameter of the collar portion 34, i.e. the distance between the first and second side edges 50, 52.

In this embodiment the collar portions 34 include a plurality of holes 56 which aid air flow around the shaft 3 or tip 5 of the endoscope 1 and permit liquid to drain more easily from the shaft 3 and tip 5 of the endoscope 1.

The first arm 14 of the device 10 further comprises a pair of legs 58 that extend from the bridging portion 42 in a direction substantially towards the second arm 16. The legs 58 extend from the bridging portion 42 proximate the side edges 50, 52 of the collar portion 34 such that a gap 60 is defined between the legs 58 and the distance between the legs 58 is substantially equal to the internal diameter of the collar portion 34.

Each of the legs 58 has a first surface 62 facing in a direction substantially towards the guard portion 12, and an opposing second surface 64 facing in a direction substantially away from the guard portion 12. A first part of latching means is provided on the legs 58 and is arranged to engage with a second part of the latching means provided on the second arm 16. In this example the first part of the latching means comprises a detent 66 in the form of a projection 66 extending from the first surface 62 of each of the legs 58. In this example each leg 58 includes two projections 66 spaced apart along a length of the leg 58. It will be appreciated, however, that in other embodiments each leg may comprise only one detent, or each leg may include more than two detents spaced apart along the length of the leg. In some embodiments the first part of the latching means comprises a ratchet.

On the second arm 16, a pair of shoulders 68 is defined where the second end 40 of the collar portion 34 meets the bridging portion 42. The shoulders 68 form the second part of the latching means and are arranged to engage with the detents 66 on the legs 58 of the first arm 14.

At least the cover plate 20 and the legs 58 of the protector device 10 are resilient so that each of the guard portion 12 and legs 58 may be elastically deformed in use. In preferred embodiments the protector device 10 is made of a substantially rigid plastics material, such as polypropylene, and the device 10 is preferably made as a single piece by injection moulding.

Figure 6:
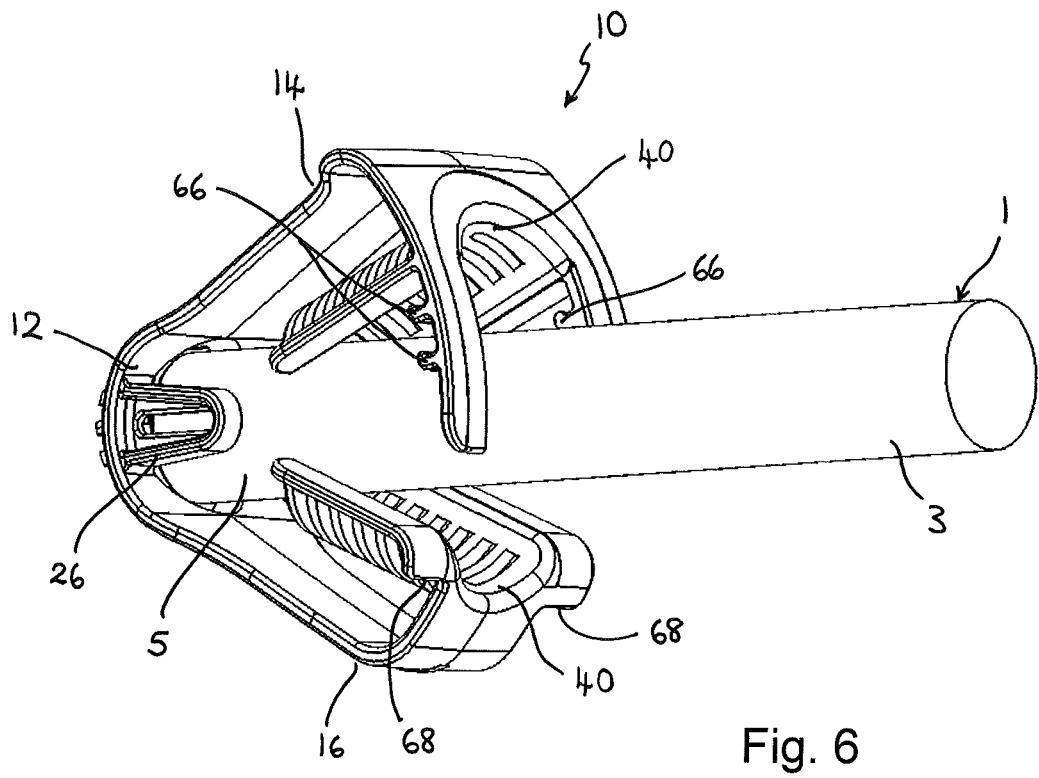
FIG. 6 is a perspective view showing an endoscope tip located in the protector device of FIG. 1, with the device in an open configuration.
Figure 7:
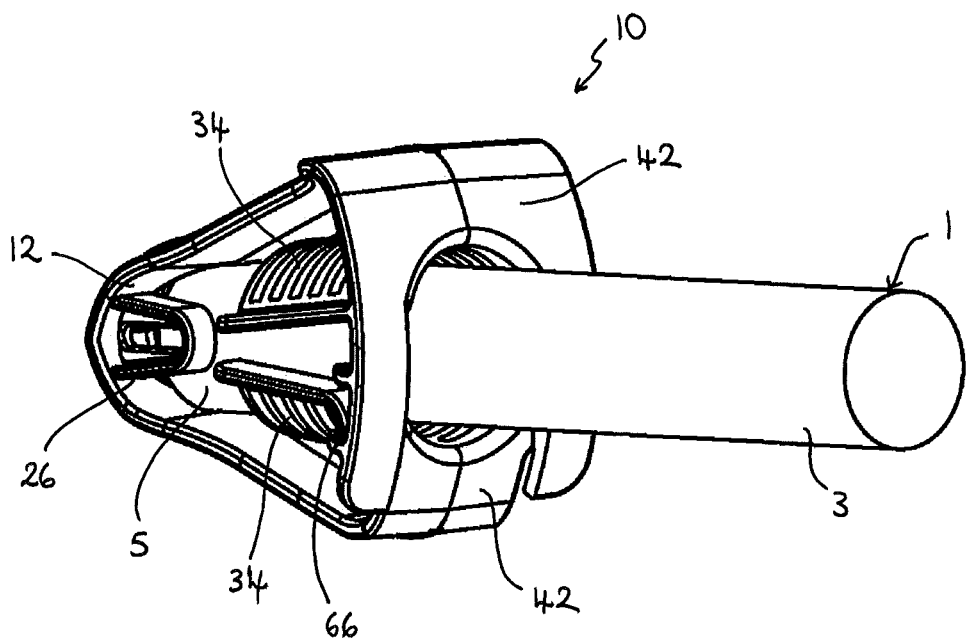
FIG. 7 is a perspective view showing an endoscope tip located in the protector device of FIG. 1, with the device in a closed configuration.

In use the first and second arms 14, 16 are movable between a first position, shown in FIGS. 1 to 6, in which there is a first distance between the second ends 40 of the collar portions 34, and a second position, shown in FIG. 7, in which the first and second parts of the latching means are engaged and there is a second distance between the second ends 40 of the collar portions 34, the second distance being smaller than the first distance. In the second position the collar portions 34 of each of the arms 14, 16 are arranged such that they together define a substantially cylindrical or conical space for receiving the shaft 3 of an endoscope 1.

In this way, the device 10 is movable between a first open position in which a tip 5 of an endoscope 1 may be inserted into the device 10 and removed from the device 10, as shown in FIG. 6, and a second closed position in which at least a part of each of the collar portions 34 grip the shaft 3 or tip 5 of the endoscope 1 to retain the device 10 on the endoscope 1, as shown in FIG. 7. Accordingly the collar portions 34 form gripping means of the device 10.

The protector device 10 is preferably configured such that the device 10 is biased into the first, open position. To retain the device 10 in the second, closed position a detent 66 on each of the legs 58 is engaged with the corresponding shoulder 68 on the second arm 16. In this position, the legs 58 extend either side of the endoscope tip 5, such that the tip 5 is located in the gap 60 between the legs 58. In embodiments in which the legs 58 include a plurality of detents 66, the detent 66 that is engaged with the shoulder 68 may be selected so as to achieve the required diameter of the cylindrical space between the collar portions 34 so that at least a part of the collar portions 34 grip the shaft 3 or tip 5 of the endoscope 1. In this way, the device 10 may be adapted to be secured to a range of endoscopes 1 having shafts 3 of different diameters.

It will be appreciated that in other embodiments other latching means may be used such as clips, hooks or interengaging teeth. Preferably, however, the latching means are integral with the first and second arms 14, 16 so that additional parts are not required that could become separated from the main body 18 of the device 10.

The protector device 10 is removed from the tip 5 of an endoscope 1 by elastically deforming the legs 58 such that the detents 66 are disengaged from the shoulders 68.

In some embodiments it may be desirable if the latching means are single use such that once the protector device 10 has been used once and the latching means have been disengaged, they cannot be re-engaged. This prevents the protector device 10 being used on multiple endoscopes thereby removing the possibility of cross-contamination.

Figure 8:
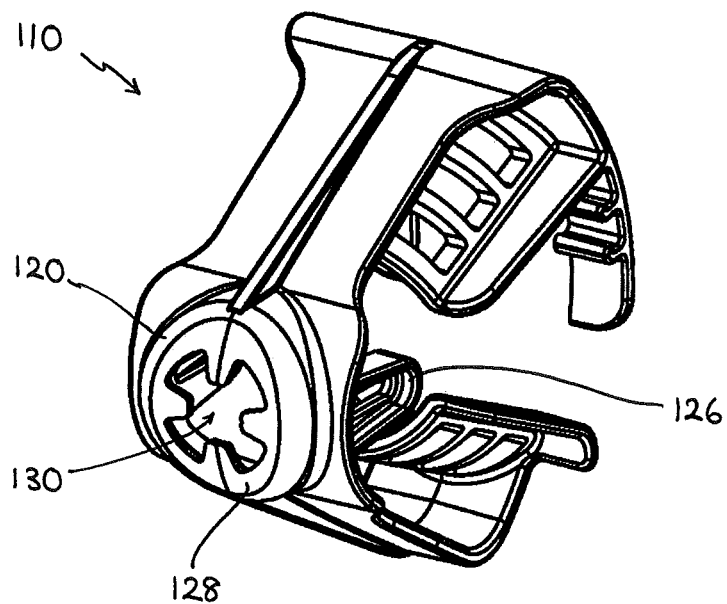
FIG. 8 is a perspective view of a protector device according to a second preferred embodiment of the present invention.

A second embodiment of a tip protector device 110 is illustrated in FIG. 8. Features that are the same as or equivalent to features of the protector device 10 of the first embodiment have been indicated with reference numerals incremented by 100. This embodiment of the protector device 110 is substantially the same as the protector device 10 of the first embodiment and like features will not be described further in relation to this embodiment.

In this embodiment at least a central region 128 of the cover plate 120 includes a single aperture 130. When an endoscope tip is located between the fingers 126, the aperture 130 allows liquids such as water to easily drain away from the tip.

Figure 9:
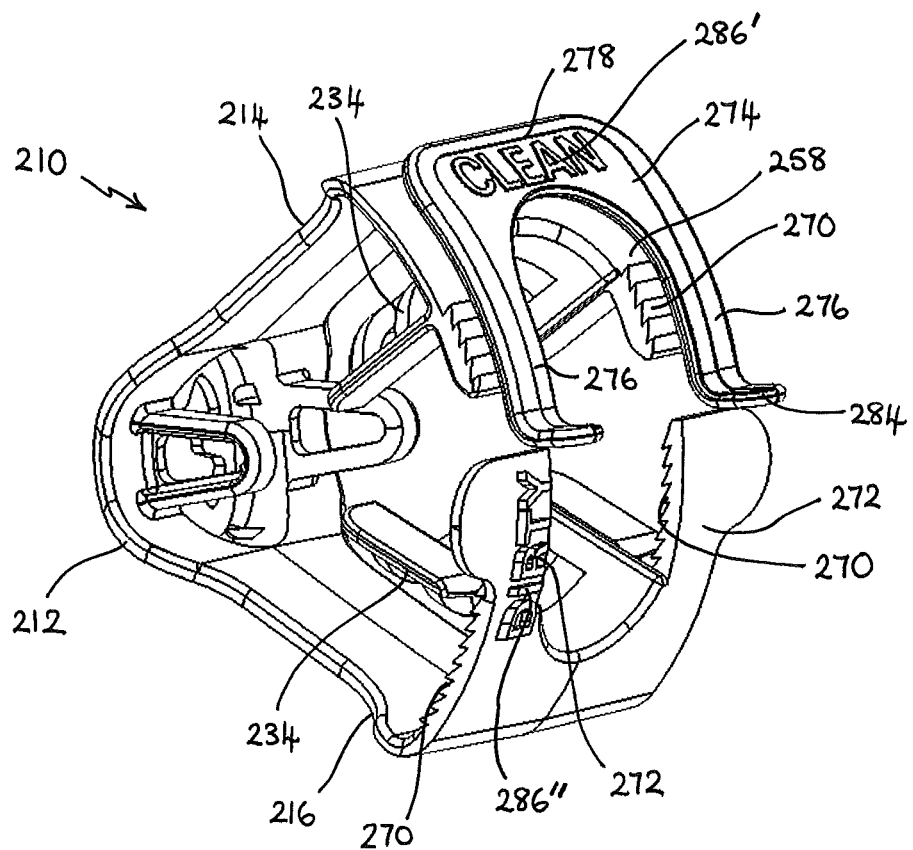
FIG. 9 is a perspective view of a tip protector device according to a third preferred embodiment of the present invention.
Figure 10:
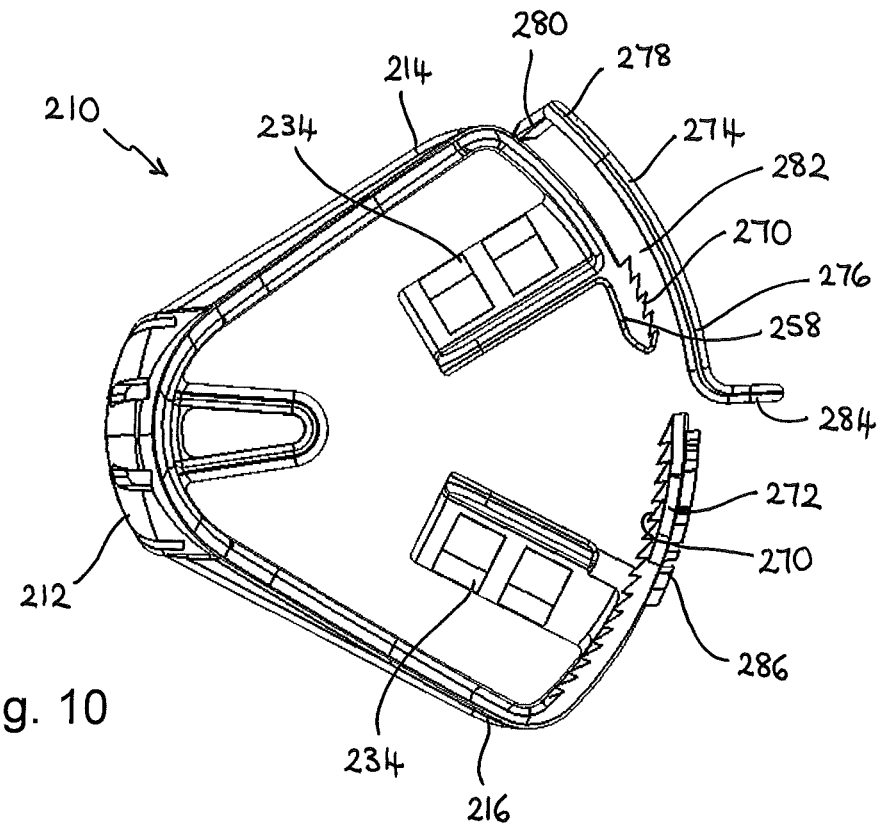
FIG. 10 is a side view of the tip protector device of FIG. 9.
Figure 11:
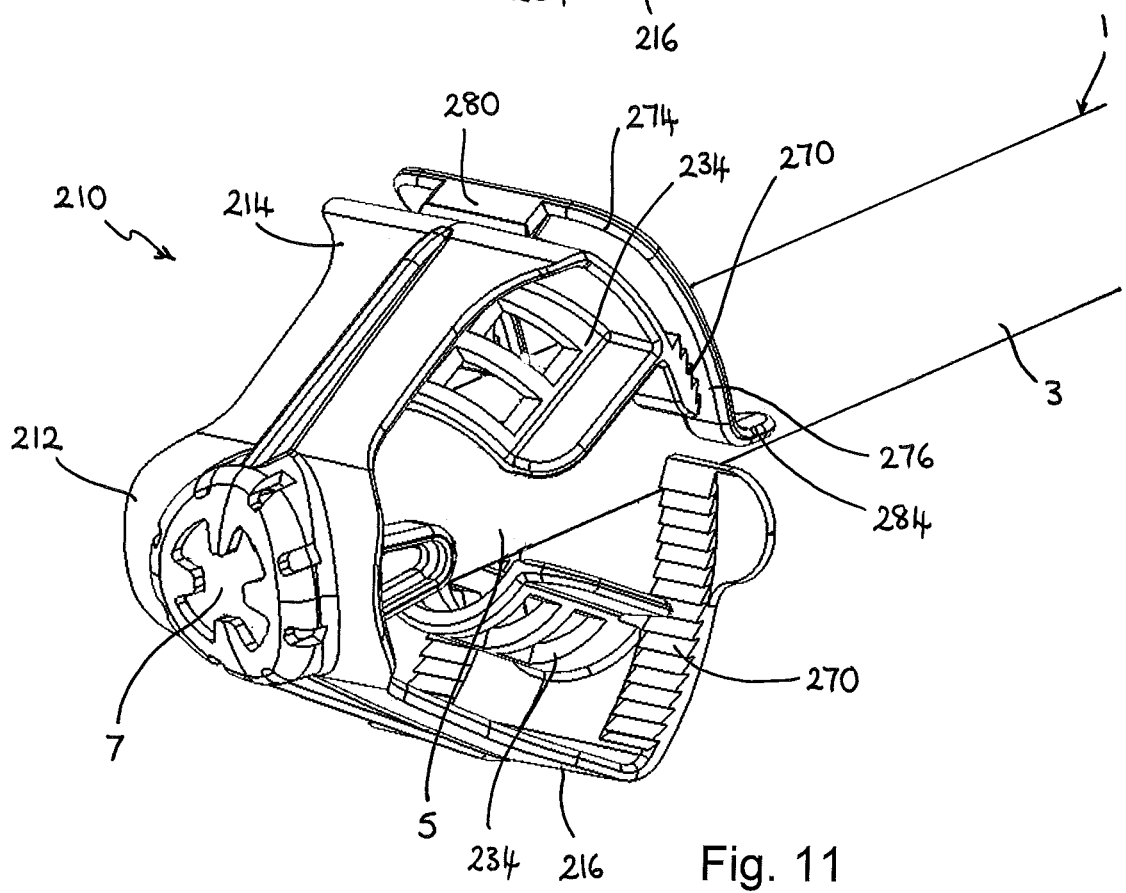
FIG. 11 is a perspective view of the tip protector device of FIG. 9 with an endoscope tip in position in the protector device, but with the protector device in an open configuration.
Figure 12:
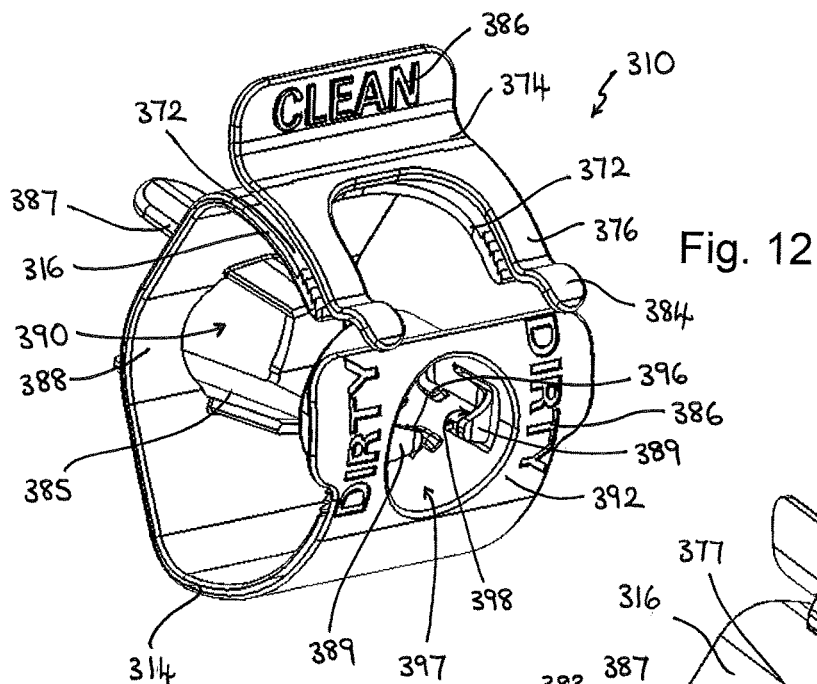
FIG. 12 is a perspective view of a tip protector device according to a fourth preferred embodiment of the present invention.
Figure 13:
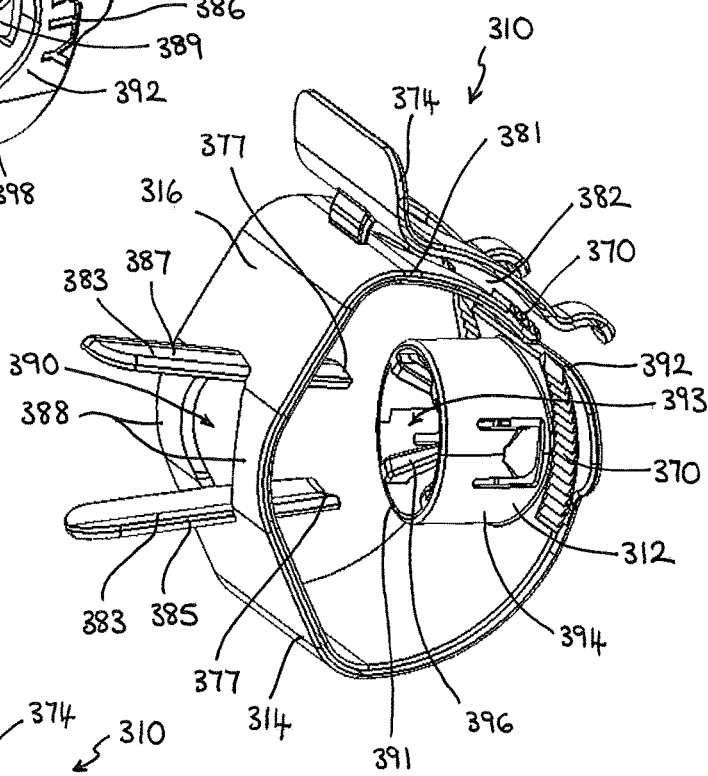
FIG. 13 is a perspective view from the side of the tip protector device of FIG. 12.
Figure 14:
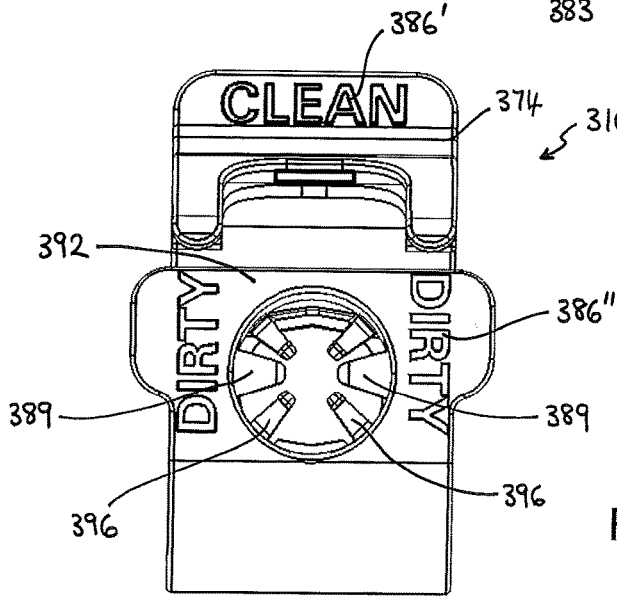
FIG. 14 is an end view of the tip protector device of FIG. 12.
Figure 15:
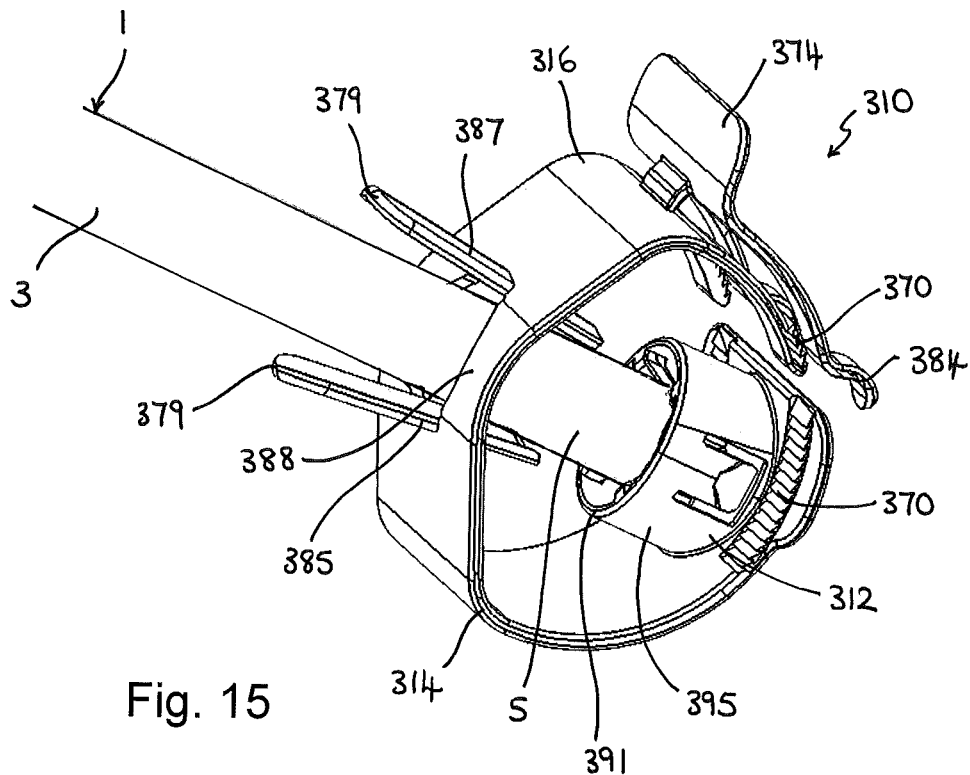
FIG. 15 is a first perspective view of the tip protector device of FIG. 12 with an endoscope tip in position in the protector device, but with the protector device in an open configuration.
Figure 16:
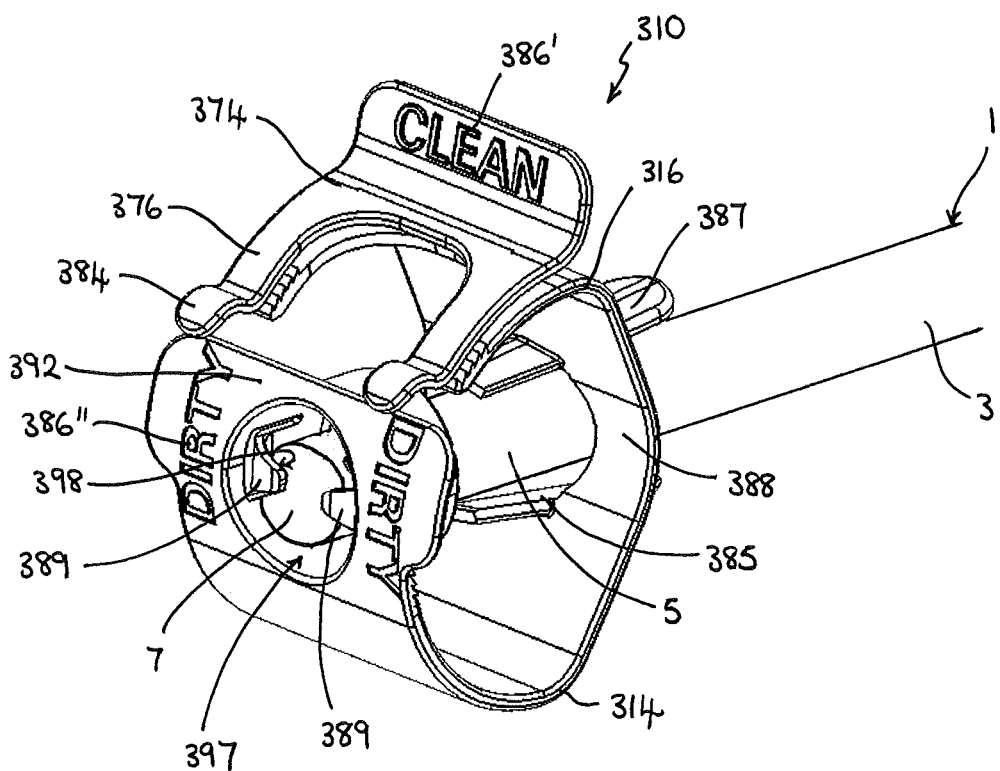
FIG. 16 is a second perspective view of the tip protector device of FIG. 12 with an endoscope tip in position in the protector device, but with the protector device in an open configuration.

A third embodiment of a tip protector device 210 is shown in FIGS. 9 to 11. The tip protector is substantially the same as the protector devices 10, 110 of the first and second embodiments and like features will not be described in detail in relation to this embodiment.

The tip protector device 210 comprises a guard portion 212, a first connection member 214 extending from a first edge of the guard portion 212 and a second connection member 216 extending from an opposite second edge of the guard portion 212. The connection members 214, 216 and guard portion 212 are integral and form a main body of the tip protector 210. A first part of each of the connection members 214, 216 extends from the guard portion 212 such that the first part of each of the connection members 214, 216 and the guard portion 212 form a substantially U-shaped or V-shaped portion of the main body.

Second parts of the connection members 214, 216 furthest from the guard portion 212 extend in directions substantially towards each other. Collar portions 234 extend from each of the second parts of the connection members 214, 216 in a direction substantially towards the guard portion 212. The collar portions 234 are the same as those of the first embodiment and will not be described further here. The collar portions 234 form gripping means that grip the shaft 3 of the endoscope 1 when the tip protector 210 is in an engaged or gripping position.

The second parts of the connection members 214, 216 further comprise latching means arranged to engage to secure ends of the connection members 214, 216 together once the tip protector 210 has been placed around the tip 5 of an endoscope 1. In this embodiment the latching means comprises complementary teeth 270 having a sawtooth profile that engage to retain the tip protector 210 in the gripping configuration.

In particular, the end of each of the connection members 214, 216 comprises a pair of leg members 258, 272. The leg members of each pair 258, 272 extend parallel to each other and are spaced apart so as to receive the shaft 3 of the endoscope 1 between them. A toothed surface 270 is provided on each of the leg members 258, 272.

When the connection members 214, 216 are moved towards each other, to move the tip protector 210 from a disengaged position to a gripping position, the sawtooth profile of the teeth 270 is such that the teeth 270 on each of the connection members 214, 216 are able to slide over each other. When the force is removed from the connection members 214, 216, the teeth 270 engage or latch together so that the tip protector 210 is retained in the gripping position.

By providing a plurality of teeth 270 on each of the connection members 214, 216 the connection members 214, 216 can be pressed together until the collar portions 234 grip the shaft 3 of the endoscope 1. In this way, the tip protector 210 is able to accommodate different sizes of shaft 3.

The tip protector 210 further comprises a tab 274 attached to the first connection member 214. The tab 274 comprises two leg portions 276 that are joined together at a first end 278 of the tab 274. The tab 274 is attached to the connection member 214 at the first end 278 by a spacing element 280 such that the leg portions 276 extend over the leg members 258 of the connection member 214. The connection between the tab 274 and the connection member 214 and in particular a size of the spacing element 280 is such that a gap 282 is defined between the leg portions 276 of the tab 274 and the leg members 258 of the connection member 214. The gap 282 is sized to receive the leg members 272 of the second connection member 216 when the tip protector 210 is moved into the gripping position.

The leg portions 276 of the tab 274 extend beyond the leg members 258 of the connection member 214 and each end of the leg portions 276 comprises a gripping lug 284. Each gripping lug 284 extends substantially perpendicularly from the tab 274 in a direction away from the connection member 214 to allow a user to grip the lug 284 and break the tab 274 as described below.

The location of the tab 274 is such that the tab 274 conceals the latching means when the first and second connection members 214, 216 are in the gripping position. Furthermore, the position of the tab 274, and in particular the leg positions 276 of the tab 274, means that the connection members 214, 216 cannot be moved with respect to each other to disengage the interengaged teeth 270 of the latching means. To allow the latching means to be disengaged the tab 274 must be broken by pulling on the lugs 284 to move the leg portions 276 away from the leg members 258 of the connection member 214. Pulling on the lugs 284 in this way at least partially breaks the attachment of the tab 274 to the connection member 214.

In preferred embodiments the attachment of the tab 274 to the connection member 214 is such that the tab 274 remains connected to the connection member 214 after the tab 274 has been broken. This may be achieved by providing a line of weakness in the spacing element 280. The spacing element 280 supports the tab 274 in a fixed position relative to the connection member 214 until a user pulls on the lugs 284 with sufficient force as to break the spacing element 280 along the line of weakness. The line of weakness, however, does not extend through the full width of the spacing element 280 so that the spacing element 280 becomes a live hinge after the tab 274 has been broken. In other embodiments the spacing element may be a live hinge and an additional support element may be provided that supports the tab in a fixed position during use of the tip protector and which is then broken when a user applies sufficient force to the lugs.

The tip protector 210 preferably comprises distinguishing means 286. The distinguishing means 286 are provided to allow a user to determine whether the tip protector 210 has been engaged with a clean and/or a dirty endoscope. For example, the tip protector 210 may be attached to a clean endoscope after sterilisation with a first distinguishing means 286' being displayed. When the endoscope is to be used in a medical procedure, the tip protector is removed and in doing so a second distinguishing means 286" is displayed. The tip protector can then be placed back on the used, dirty endoscope with the second distinguishing means 286" being displayed. The distinguishing means 286 are configured such that the second distinguishing means 286" displays to a user that the tip protector has been used on a dirty endoscope and should not be subsequently placed on a clean endoscope.

In this embodiment a first distinguishing means 286' is provided on the tab 274 attached to the first connection member 214 and a second distinguishing means 286" is provided on the second connection member 216. The first and second distinguishing means 286', 286" are different to allow them to be distinguished. The position of the second distinguishing means 286" is such that the second distinguishing means 286" is concealed by the tab 274 when the first and second connection members 214, 216 are in the gripping position. When the tab 274 is broken the second distinguishing means 286" is then revealed.

The first distinguishing means 286' may comprise the word CLEAN and the second distinguishing means 286" may comprise the word DIRTY. In other embodiments the distinguishing means 286 may comprise any other suitable symbols, letters, numbers or other graphical devices. For example, the first distinguishing means 286' may comprise an area having a first colour such as green and the second distinguishing means 286" may comprise an area having a second colour such as red.

A fourth embodiment of a tip protector device 310 according to the present invention is shown in FIGS. 12 to 16.

The tip protector 310 comprises a first connection member 314 and a second connection member 316. In this embodiment each of the first and second connection members 314, 316 are curved. The connection members 314, 316 are joined at their respective first ends by a pair of bridging members 388. The bridging members 388 are spaced apart across a width of the connection members 314, 316 such that an opening 390 is defined and bounded by the first ends of the connection members 314, 316 and the bridging members 388. The opening 390 is sized to receive the shaft 3 of an endoscope 1.

Typically the bridging members 388 and connection members 314, 316 are integrally formed.

Furthermore, an outer edge of a first one of the bridging members 388 is preferably continuous with a first edge of each of the connection members 314, 316 and an outer edge of a second one of the bridging members 388 is preferably continuous with a second edge of each of the connection members 314, 316.

A guard portion 312 is located at the second end 392 of the first connection member 314. The guard portion 312 comprises a collar 394, guide fingers 396 and an abutment surface 398. The collar 394 comprises an annular wall 395 that extends from the connection member 314 in a direction towards the opening 390. The connection member 314 includes an aperture 397 that is surrounded by the annular wall 395. Resilient guide fingers 396 extend from an internal surface 393 of the annular wall 395, and preferably a plurality of guide fingers 396 are located spaced apart around the collar 394. The guide fingers 396 are connected to the internal surface 393 of the wall 395 proximate a free end edge 391 of the wall 395. The fingers 396 extend inwardly and in a direction towards the aperture 397 in the connection member 314.

The diameter of the annular wall 395 is such that the tip 5 of an endoscope 1 may be inserted into the collar 394. As the tip 5 is inserted, the guide fingers 396 are pushed outwards towards the surface 393 of the annular wall 395. The guide fingers 396 are biased so that they apply a force to the tip 5 of the endoscope 1 and act to centre the tip 5 within the collar 394. The length and resilience of the guide fingers 396 are such that tips 5 of different diameters may be held within the collar 394.

The abutment surface 398 prevents the tip 5 of the endoscope 1 being pushed through the aperture 397 in the connection member 314. In this embodiment the abutment surface 398 is provided by a pair of stop members 389 that extend radially inwardly from the internal surface 393 of the collar wall 395. When an endoscope tip 5 is inserted into the collar 394 an end of the tip 5 contacts the abutment surface 398 to prevent the tip protector 310 being pushed further along the shaft 5 of the endoscope 1. The end face 7 is therefore retained in the guard portion 312 such that a part of the guard portion 312 extends distally of the end face 7. The recessed end face 7 is, therefore, protected from any knocks. The stop members 389 preferably only contact an edge region of the end face 7 of the endoscope 1 so that no contact is made with a central region of the end face 7.

Gripping means are located at the first ends of the connection members 314, 316. In this embodiment the gripping means comprises first and second gripping members 385, 387. The first gripping member 385 is connected to the first end of the first connection member 314 and the second gripping member 387 is connected to the first end of the second connection member 316, so that the gripping members 385, 387 are opposite each other across the opening 390. Each of the gripping members 385, 387 comprises an elongate arm 383 extending between first and second ends 377, 379. The arms 383 are substantially planar, however, the arms 383 may be curved to complement and accommodate the curvature of the cylindrical shaft 3 of the endoscope Each of the gripping members 385, 387 is attached to the end of the respective connection member 314, 316 approximately midway along the length of the gripping member 385, 387. A first portion of each of the gripping members 385, 387, between the respective connection member 314, 316 and the first end 377, extends towards the guard portion 312 and a second portion of each of the gripping members 385, 387, between the respective connection member 314, 316 and the second end 379, extends in an opposite direction away from the guard portion 312.

A second end 381 of the second connection member 316 comprises two leg members 372. The leg members 372 are spaced apart across the width of the connection member 316.

To attach the tip protector 310 to the tip 5 of the endoscope 1, the second ends 392, 381 of the first and second connection members 314, 316 are moved towards each other. The spacing of the leg members 372 is such that they extend either side of the collar 394 of the guard portion 312 when the tip protector 310 is in the gripping position.

Latching means in the form of complementary teeth 370 are provided on the leg members 372 of the second connection member 316 and at the second end 392 of the first connection member 314 either side of the collar 394.

Movement of the first and second connection members 314, 316 into the gripping position also causes the first ends 377 of the gripping members 385, 387 to get closer together. The gripping members 385, 387, therefore, grip the shaft 3 of the endoscope 1 between them.

The first and second connection members 314, 316 are, therefore, squeezed together until the first portions of the gripping members 385, 387 grip the shaft 3 of the endoscope 1. The interengaged teeth 370 of the latching means retain the tip protector 310 in this position to retain the tip protector 310 on the tip 5 of the endoscope 1.

A tab 374 is attached to the second connection member 316. The tab 374 is substantially the same as the tab 274 of the previous embodiment and will not be described in detail in relation to this embodiment. The tab 374 is attached to the connection member 316 such that leg portions 376 of the tab 374 extend over the leg members 372 of the connection member 316. The connection between the tab 374 and the connection member 316 is such that a gap 382 is defined between the leg portions 376 of the tab 374 and the leg members 372 of the connection member 316. The gap 382 is sized to receive regions of the second end 392 of the first connection member 314 either side of the collar 394 when the tip protector 310 is moved into the gripping position.

The location of the tab 374 is such that the tab 374 conceals the latching means when the first and second connection members 314, 316 are in the gripping position. To allow the latching means to be disengaged the tab 374 must be broken by pulling on lugs 384 of the tab 374 to move the leg portions 376 away from the leg members 372 of the connection member 316. Pulling on the lugs 384 in this way at least partially breaks the attachment of the tab 374 to the connection member 316, as described above in relation to the third embodiment.

The tip protector 310 preferably comprises distinguishing means 386. In this embodiment a first distinguishing means 386' is provided on the tab 374 attached to the second connection member 316 and a second distinguishing means 386" is provided on the first connection member 314. The first and second distinguishing means 386', 386" are different to allow them to be distinguished. The position of the second distinguishing means 386" is such that the second distinguishing means 386" is concealed by the tab 374 when the first and second connection members 314, 316 are in the gripping position. When the tab 374 is broken the second distinguishing means 386" is then revealed.

To move the tip protector 310 back to the disengaged position the latching means are disengaged and the first and second connection members 314, 316 are moved apart to release the gripping means from the shaft 3 of the endoscope 1. In this embodiment movement of the second portions of the gripping members 385, 387 towards each other causes the first portions of the gripping members 385, 387 to move apart and, additionally, due to the connection of the gripping members 385, 387 to the connection members 314, 316, causes the second ends 392, 381 of the connection members 314, 316 to move apart. Removal of the tip protector 310 from the tip 5 of the endoscope 1 may therefore be aided by a user pressing the second ends 379 of the gripping members 385, 387 towards each other to release the grip on the shaft 3.

A fifth embodiment of a tip protector device 410 according to the invention is shown in FIGS. 18 to 22. The protector device 410 comprises a guard portion 412, a first connection member or arm 414 and a second connection member or arm 416. The protector device 410 is of unitary, one-piece construction, and is formed from a flat sheet of material. In this example the protector device 410 is formed from a blank 511 having the shape shown in FIG. 17.

The blank 511 includes a first arm panel 513, a second arm panel 515 and first and second guard panels 517, 519. A first fold line 521 is located between the first arm panel 513 and the second arm panel 515, a second fold line 523 is located between the second arm panel 515 and the first guard panel 517, and a third fold line 525 is located between the first guard panel 517 and the second guard panel 519. The first, second and third fold lines 521, 523, 525 are substantially parallel to each other.

A first pair of hinge panels 527 extends between the first arm panel 513 and the second arm panel 515 and a second pair of hinge panels 529 extends between the second arm panel 515 and the first guard panel 517.

Each of the first and second arm panels 513, 515 includes an aperture 531, 533. The apertures 531, 533 may be circular or may be elongate, having a stadium shape for example. At least a part of the edge of each of the apertures 531, 533 is preferably curved. The apertures 531, 533 are sized to receive the shaft 3 of an endoscope 1.

A plurality of holes 535 are provided in one or both of the first and second guard panels 517, 519. In this example three elongate holes 535 are provided spanning the third fold line 525 so that a part of each hole 535 is located in the first guard panel 517 and a part of each hole 535 is located in the second guard panel 519. In other embodiments holes may be provided in only the first guard panel 517, only the second guard panel 519, or in both guard panels 517, 519.

Securing means are provided on the second guard panel 519 and the second arm panel 515 to enable a part of the second guard panel 519 to be secured to the second arm panel 515. In this example the securing means comprises a tab 537 extending from the second guard panel 519 and a slot 539 formed in the second arm panel 515. The tab 537 includes a portion having the shape of an arrow head.

In the illustrated embodiment retaining means are provided on the second pair of hinge panels 529 and the second guard panel 519. The retaining means comprises a tab portion 541 of each one of the second pair of hinge panels 529 and a corresponding pair of slots 543 formed in the second guard panel 519.

Figure 17:
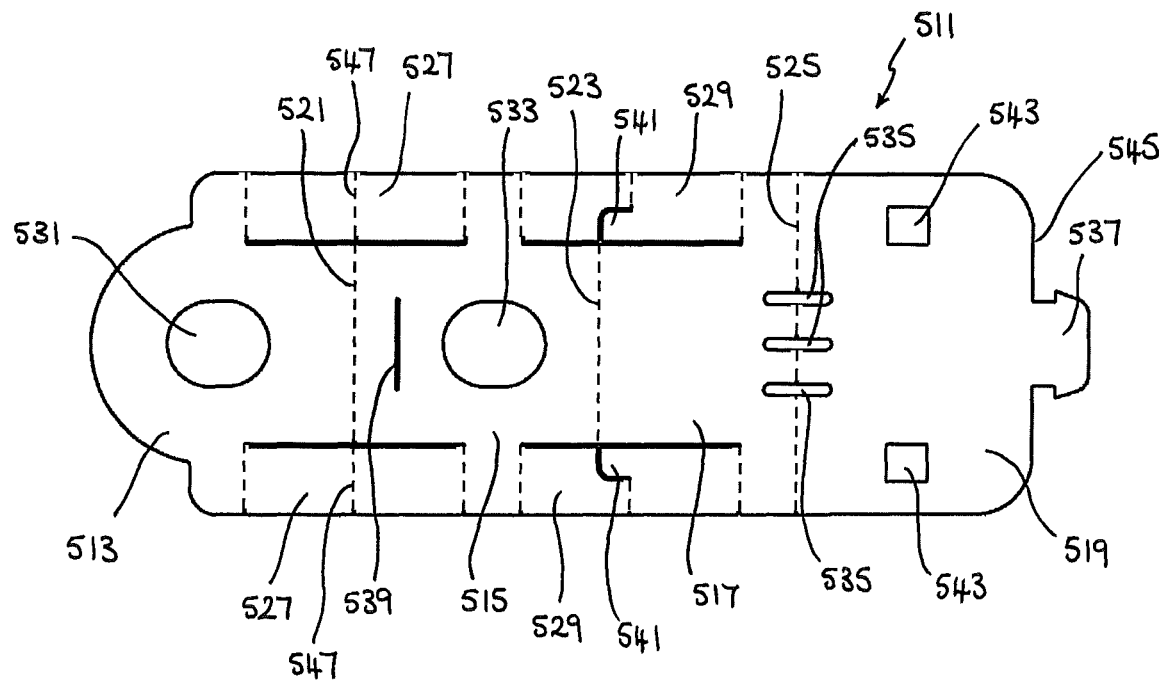
FIG. 17 is a plan view of a blank for forming a protector device according to a fifth preferred embodiment of the present invention.

The protector device 410 is formed by folding along the fold lines of the blank 511, illustrated in FIG. 17 by dashed lines. In particular, the blank 511 is folded along the first and second fold lines 521, 523 such that the first and second arm panels 513, 515 and the first guard panel 517 form a concertina shape. The blank 511 is also folded along the third fold line 525 such that the tab 537 extending from an end edge 545 of the blank 511 can be inserted through the slot 539 in the second arm panel 515. In this way the second arm panel 515 and the first and second guard panels 517, 519 form a generally triangular shaped part of the protector device 410.

The tab portions 541 of each of the second pair of hinge panels 529 are engaged with the corresponding pair of slots 543 such that the hinge panels 529 extend between the second arm panel 515 and the first and second guard panels 517, 519.

Figure 18:
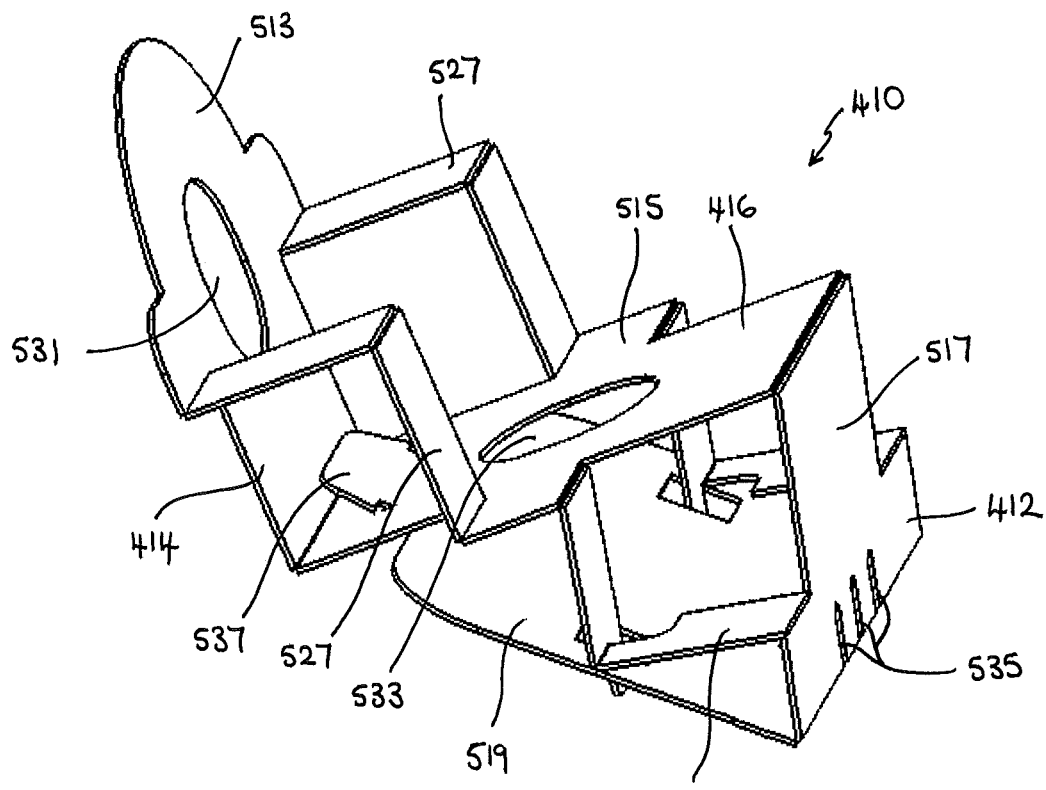
FIG. 18 is a first perspective view of the protector device formed from the blank of FIG. 17.
Figure 19:
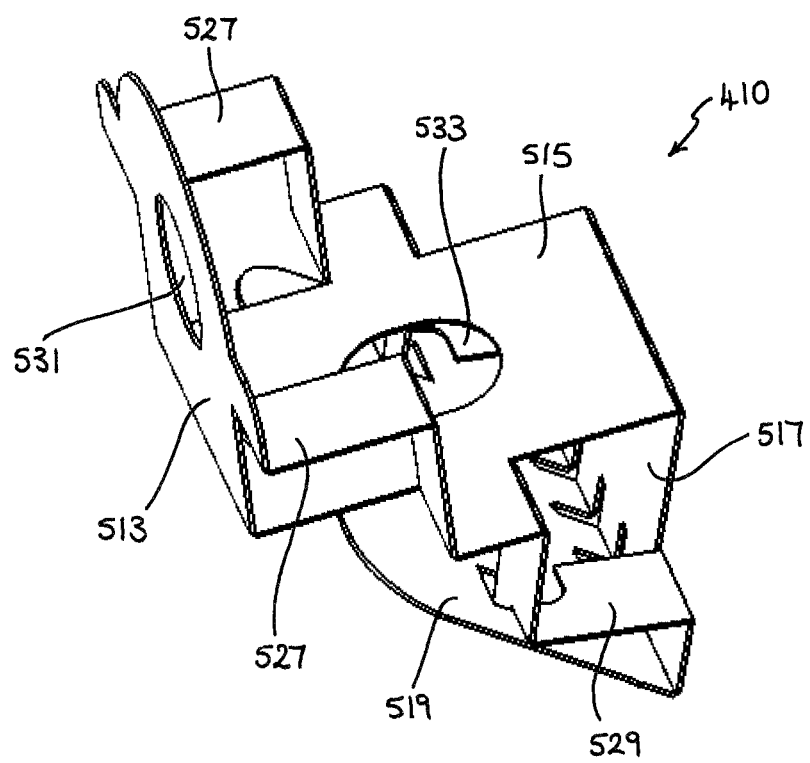
FIG. 19 is a second perspective view of the protector device of FIG. 18.
Figure 20:
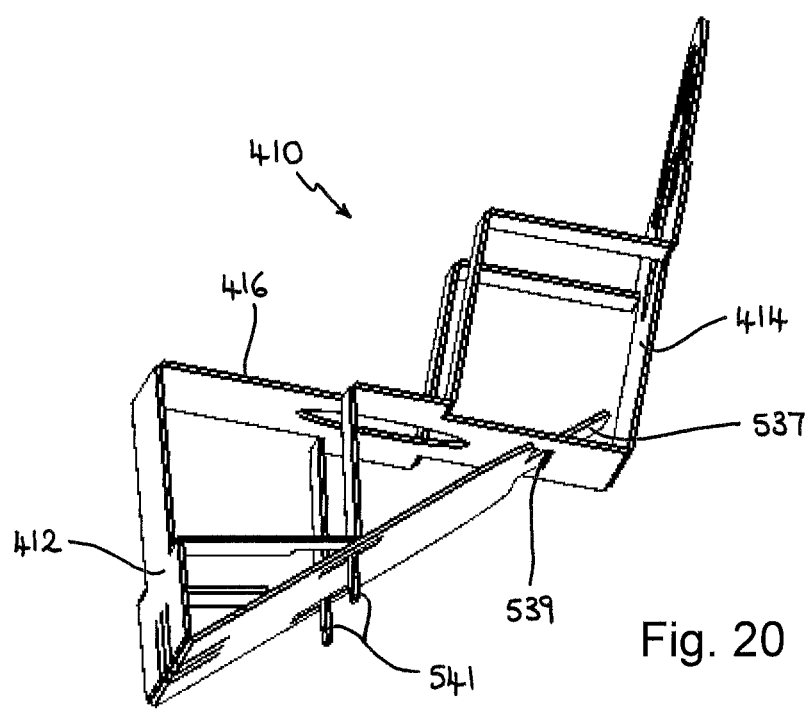
FIG. 20 is a third perspective view of the protector device of FIG. 18.

Each of the first pair of hinge panels 527 includes a central fold line 547 which is folded in an opposite direction to the first fold line 521. The arrangement of the first and second arm panels 513, 515 and the first pair of hinge panels 527 is preferably such that there is an angle of about 90° between the first and second arm panels 513, 515 when the protector device 410 is assembled, as shown in FIGS. 18 to 20.

In the assembled state, the first arm panel 513 forms the first arm 414 of the protector device 410, the second arm panel 515 forms the second arm 416 of the protector device 410 and the first and second guard panels 517, 519 together with the second pair of hinge panels 529 form the guard portion 412 of the protector device 410.

The fold along the first fold line 521 and/or the first pair of hinge panels 527 are preferably configured such that a biasing force is applied to the first and second arms 414, 416 in a direction so as to increase the angle between the first and second arms 414, 416.

Figure 21:
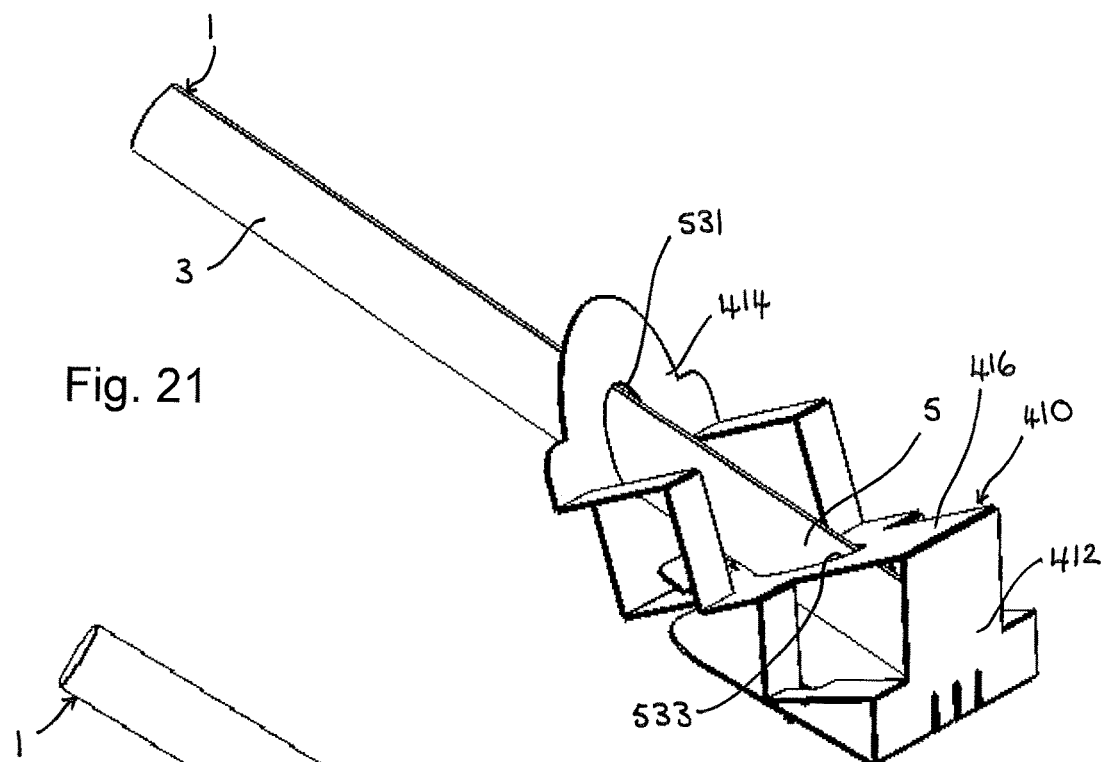
FIG. 21 is a perspective view of the protector device of FIG. 18 engaged with a tip of an endoscope.
Figure 22:
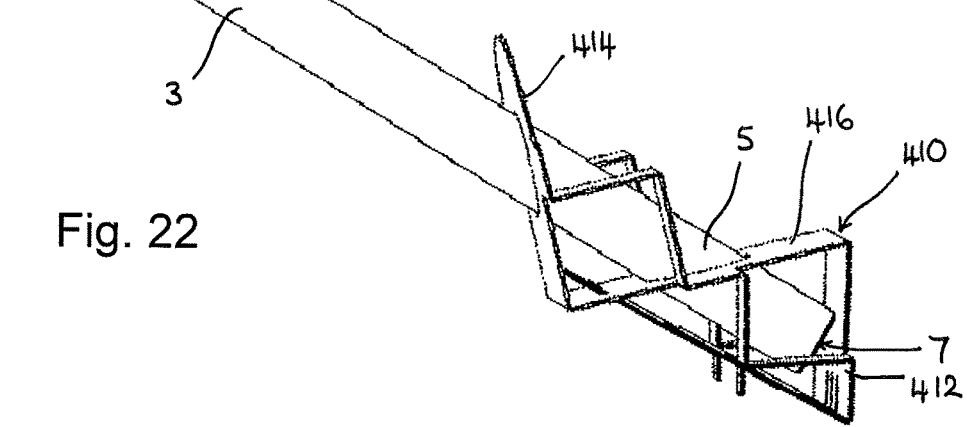
FIG. 22 is a further perspective view of the protector device and endoscope tip of FIG. 21.

In use, once the protector device 410 has been assembled, a user moves the first and second arms 414, 416 into a first position against the biasing force to decrease the angle between the arms 414, 416. The tip 5 of an endoscope 1 can then be inserted through the apertures 531, 533 in the arms 414, 416 so that the tip 5 extends into the guard portion 412 of the device 410, as shown in FIGS. 21 and 22.

Once the tip 5 is in the correct position the user can release the first and second arms 414, 416 so that the angle between them increases due to the biasing force. This in turn causes the angle of the plane of each of the arms 414, 416 with respect to the longitudinal axis of the shaft 3 of the endoscope 1 to decrease until the arms 414, 416 are in a second position.

In this second position the angles of the plane of each arm 414, 416 with respect to the longitudinal axis of the shaft 3 are such that at least a part of the edge of each of the apertures 531, 533 contacts the shaft 3 or tip 5 of the endoscope 1. This causes the protector device 410 to grip the shaft 3 or tip 5. In particular a part of each of the first and second arms 414, 416 contacts the shaft 3 or tip 5 of the endoscope 1 on opposing sides of the shaft 3 or tip 5. The edges of the apertures 531, 533 in the arms 414, 416, therefore, form part of the gripping means of this device 410.

The protector device 410 is able to accommodate different diameters of endoscope shaft 3 because the apertures 531, 533 are sized such that shafts 3 of different diameters can all be inserted through the apertures 531, 533 when the planes of the arms 414, 416 are substantially perpendicular to the longitudinal axis of the shaft 3, and because the biasing force causes the angle between the first and second arms 414, 416 to increase until parts of the arms 414, 416 at the edge of each of the apertures 531, 533 contact the shaft 3 or tip 5 so as to grip the shaft 3 or tip 5.

With the protector device 410 retained on the tip 5 of the endoscope 1 the end face 7 of the tip 5 is located within the guard portion 412, and in particular, in this example, a part of each of the first and second guard panels 517, 519 extend across the end face 7 to protect it.

The holes 535 formed in the guard panels 517, 519 allow liquids such as water to drain away from the tip 5 of the endoscope 1. Furthermore, the shape of the guard portion 412 is such that minimal or no contact is made between the guard portion 412 and the end face 7 of the tip 5.

The second pair of hinge panels 529 and at least a part of each of the first and second guard panels 517, 519 prevent knocks to the side of the tip 5 of the endoscope 1 when the tip 5 is correctly positioned within the protector device 410.

To remove the protector device 410 from the tip 5 of the endoscope 1, a user moves the first and second arms 414, 416 back into the first position and withdraws the tip 5 through the apertures 531, 533.

Figure 23:
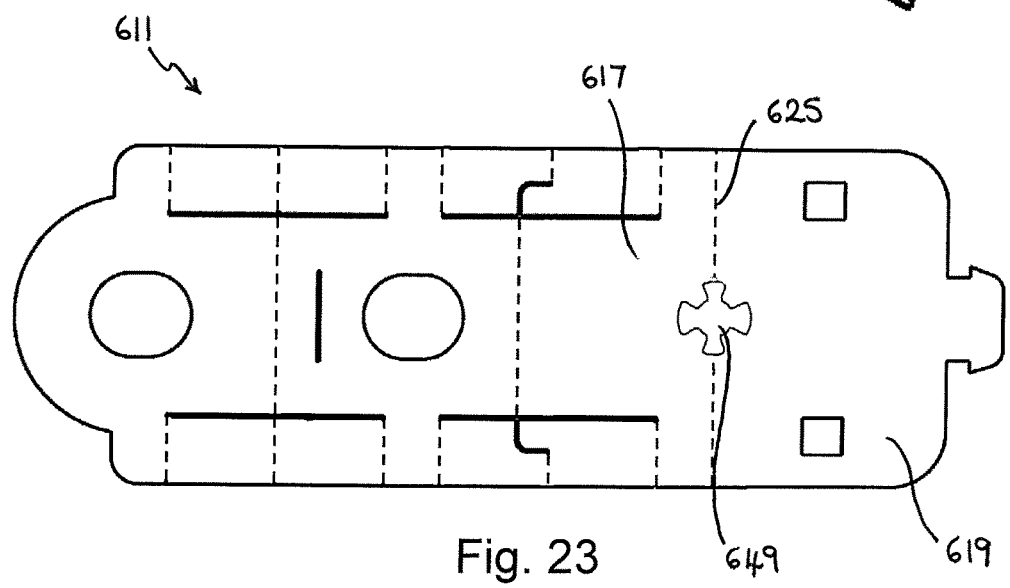
FIG. 23 is a plan view of a blank for forming a protector device according to a sixth preferred embodiment of the present invention.

A blank 611 for constructing a sixth embodiment of a protector device is illustrated in FIG. 23. This embodiment of a blank is substantially the same as the blank 511 used to form the fifth embodiment of the protector device 410 and like features will not be described further in relation to this embodiment.

In this embodiment the blank 611 comprises a single hole 649 spanning the third fold line 625 so that a part of the hole 649 is located in the first guard panel 617 and a part of the hole 649 is located in the second guard panel 619. In other embodiments a single hole may be provided in only the first guard panel 617, only the second guard panel 619, or in each of the guard panels 617, 619.

Although in FIGS. 8 and 23 the aperture 130 or hole 649 has been shown as having a general cross shape, it will be appreciated that in other embodiments the hole or aperture may be of any shape. In preferred embodiments the hole or aperture is substantially circular.

A feature of the tip protector devices of the present invention is that the devices grip the endoscope shaft 3 or tip 5 at a distance from the end face 7. In this way there is a region or length of the tip 5 between the end face 7 and the gripping means which is not gripped by the protector device.

The protector devices of the present invention are typically sized to receive and grip an endoscope 1 having a shaft 3 with a diameter of between about 2 mm and 10 mm.

It is desirable if the protector devices of the present invention include a single-use feature such that the device cannot be reused. This feature is preferably designed to break, or in some other way become inoperable, after the protector device has been used for a first time, such that the device cannot be retained in the second position for a second time, thereby preventing the device from gripping a second endoscope shaft.

Although the tip protector devices described above have been described in connection with their application to an endoscope tip, it will be appreciated that the tip protector devices may be attached to the tip of any instrument having an elongate shaft where it is desired to protect the tip, and in particular an end face, of the instrument.

The present invention, therefore, provides an improved tip protector device that overcomes at least some of the disadvantages of prior art devices.

The invention claimed is:

1. A tip protector device for an instrument, the instrument comprising an elongate shaft having a distal tip and said tip including an end face, and the tip protector device comprising:
   a guard portion engagable with said tip, the guard portion including an abutment surface arranged to contact the tip such that a part of the guard portion extends distally of said end face, and the guard portion being configured to prevent contact between the guard portion and a central portion of the end face;
   a first gripping member and a second gripping member, the gripping members being arranged to grip a part of the shaft of the instrument at a distance from said end face;
   a first connection member;
   a second connection member, the first gripping member extending from an end of the first connection member and the second gripping member extending from an end of the second connection member, the first and second connection members being movable relative to each other between a first, disengaged position in which said tip of the instrument can be inserted into and removed from the tip protector device, and a second, gripping position in which the gripping members contact and grip the shaft of the instrument, and
   the first and second connection members being biased into the first position; and
   latching means configured to retain the first and second connection members in the second position.

2. A tip protector device as claimed in claim 1, wherein the protector device is a unitary body having a one piece construction.

3. A tip protector device as claimed in claim 1, wherein the guard portion comprises at least one aperture.

4. A tip protector device as claimed in claim 1, wherein the protector device is made from a plastics material.

5. A tip protector device as claimed in claim 1, wherein a first part of the latching means is provided on the first connection member and a second part of the latching means is provided on the second connection member.

6. A tip protector device as claimed in claim 5, wherein the first connection member extends between a first gripping member at a first end and the first part of the latching means at a second end and the second connection member extends between a second gripping member at a first end and the second part of the latching means at a second end, and a bridging member joins the first and second connection members at their respective first ends so that the first and second gripping members are spaced apart for receiving the shaft of the instrument therebetween.

7. A tip protector device as claimed in claim 6, wherein the guard portion is located at or proximate the second end of the first connection member.

8. A tip protector as claimed in claim 7, wherein the guard portion comprises a collar configured, in use, to surround the tip of the instrument and wherein the second end of the second connection member comprises two leg members, the leg members being spaced apart so as to receive the collar between them.

9. A tip protector device as claimed in claim 8, wherein the second part of the latching means is located on the leg members.

10. A tip protector device as claimed in claim 6, wherein each of the gripping members comprises a first portion that extends in a direction substantially towards the second end of the respective connection member and a second portion that extends in a direction substantially opposite to that of the first portion.

11. A tip protector device as claimed in claim 1, wherein the first connection member extends from a first side of the guard portion and the second connection member extends from a second side of the guard portion.

12. A tip protector device as claimed in claim 11, wherein a first part of the latching means is located at an end of the first connection member furthest from the guard portion and a second part of the latching means is located at an end of the second connection member furthest from the guard portion.

13. A tip protector device as claimed in claim 12, wherein the end of the first connection member comprises two leg members, the leg members being spaced apart so as to receive the shaft of the instrument between them.

14. A tip protector device as claimed in claim 13, wherein the first part of the latching means is located on the leg members.

15. A tip protector device as claimed in claim 1, wherein each of the gripping members extends from the end of the respective connection member in a direction towards the guard portion.

16. A tip protector device as claimed in claim 1, wherein each of the gripping members is semi cylindrical.

17. A tip protector device as claimed in claim 1 wherein the latching means comprises interengaging teeth.

18. A tip protector device as claimed in claim 1 further comprising a tab attached to the first or the second connection member, the tab arranged to conceal the latching means when the first and second connection members are in the second position, and the tab being configured such that the tab must be broken to allow the latching means to be disengaged to move the first and second connection members to the first position.

19. A tip protector device as claimed in claim 18 further comprising distinguishing means, a first distinguishing means being provided on the tab and a second distinguishing means being concealed by the tab when the first and second connection members are in the second position, the second distinguishing means being revealed when the tab is broken.

20. An assembly comprising:
   a tip protector device as claimed in claim 1; and an instrument, the instrument comprising an elongate shaft having a tip and said tip including an end face, and the tip protector device being engaged with the tip of the instrument.

21. An assembly as claimed in claim 20, wherein the instrument is an endoscope.

22. An assembly as claimed in claim 20, wherein the instrument is a borescope.

* * * * *